(12) United States Patent
Stitt et al.

(10) Patent No.: US 7,823,818 B2
(45) Date of Patent: Nov. 2, 2010

(54) SYSTEM AND METHOD FOR PRODUCING WEIGHED PORTIONS OF POWDER FROM AT LEAST ONE BIOLOGICAL MATERIAL AT CRYOTEMPERATURES

(75) Inventors: Mark Stitt, Potsdam (DE); Ronan Sulpice, Potsdam (DE); Yves Gibon, Berlin (DE)

(73) Assignee: Max-Planck-Gessellschaft zur Foerderung der Wissenschafter E.V., Munich (DE)

( * ) Notice: Subject to any disclaimer, the term of this patent is extended or adjusted under 35 U.S.C. 154(b) by 444 days.

(21) Appl. No.: 11/975,129

(22) Filed: Oct. 17, 2007

(65) Prior Publication Data

US 2009/0101738 A1    Apr. 23, 2009

(51) Int. Cl.
*B02B 1/08*    (2006.01)
*B02B 5/02*    (2006.01)
*B02C 21/00*   (2006.01)

(52) U.S. Cl. .................. 241/66; 241/171; 241/175; 241/179

(58) Field of Classification Search .............. 241/2, 241/175, 171, 179, 66
See application file for complete search history.

(56) References Cited

U.S. PATENT DOCUMENTS

| 2,247,978 | A  | * | 7/1941  | Arkel ..................... 366/110 |
| 6,880,771 | B2 | * | 4/2005  | Deppermann ............... 241/2   |
| 7,448,566 | B2 | * | 11/2008 | Bysouth .................. 241/175 |
| 2003/0146313 | A1 | * | 8/2003 | Deppermann ............ 241/30  |

* cited by examiner

*Primary Examiner*—Bena Miller
(74) *Attorney, Agent, or Firm*—Ballard Spahr LLP

(57) ABSTRACT

A system and a method for producing a quantified defined portions of powder from at least one biological material at cryotemperature is shown, comprising means for grinding the biological material deposited in at least one first vessel to the powder; means for loosening the powder resulting from grinding the biological material in the first vessel; means for positioning at least one first opening in the first vessel, and means for transferring the quantified defined portions of powder in a plurality of second vessels by using the first opening as a transfer way.

13 Claims, 9 Drawing Sheets

SYSTEM AND METHOD FOR PRODUCING WEIGHED PORTIONS OF POWDER FROM AT LEAST ONE BIOLOGICAL MATERIAL AT CRYOTEMPERATURES

FIELD OF THE INVENTION

The invention relates to a system and a method for producing weighed portions of powder from at least one biological material at cryotemperatures.

BACKGROUND OF THE INVENTION

It is known that biological materials, for example plant material, are ground manually in different quantities in order to obtain plant powder. This plant powder can be used to perform expression profiling, polysome profiling, enzyme profiling, phosphor-proteomics and metabolite profiling, which are needed to perform research work in this area. However, each of the preparing steps and research steps were performed manually by using manual tools for grinding the plants and for select defined portions of the obtained powder in order to perform the mentioned research tests.

There is a need to support these research steps by technical automation, since the number of biological materials to be tested is still increasing.

Because of the characteristics of the biological material to be examined it is necessary to perform the working steps at cryotemperatures, e.g. at −60° C., which results in a complicated handling of the different steps to be performed manually.

Therefore, it is an object of the present invention, to provide a system and a method for producing portions of a powder from at least one biological material at cryotemperatures that enables the automatic performing of working steps without any manual support.

SUMMARY OF THE INVENTION

This object is solved by a system according to the features of the present invention.

According to the subject of the invention a system for producing quantified defined portions of powder from at least one biological material at cryotemperatures comprises:
  means for grinding the biological material deposited in at least one first vessel to powder;
  means for loosening the powder resulting from grinding the biological material in the first vessel;
  means for positioning at least one first opening in the first vessel; and
  means for transferring the quantified defined portions of powder into a plurality of second vessels by using the first opening as a transfer way.

A method according to the present invention includes steps of:
  grinding biological material deposited in at least one first vessel to the powder;
  loosening the powder resulting from grinding the biological material in the first vessel;
  positioning at least one first opening in the first vessel; and
  transferring the quantified defined portions of the powder into a plurality of second vessels by using the first opening as a transfer way.

By using such a system and applying such a method, it is possible to perform automatically without any manual help the grinding step, the loosening step, the positioning step and the transferring step into other vessels, which can be used to perform the profiling work steps, in an uncomplicated and fast way which provides an high output of a plurality of portions of the powder. The biological material can be a plant or other material which is to be ground.

By using such a method, a robotized system is provided to grind plant or other tissues to a fine powder and aliquot them for example into six weighed samples in micronic tube format at temperatures of for example 0° C.-100° C., in particular −70° C., with a throughput of for example 100 samples per 24 hours. It is possible to grind plant tissues with defined genetic diversities in order to receive multilevel phenotyping as for example expression arrays, robotized qRT-PCA, enzymes analyses, methabolites analyses, and fizzyology, fluxes growth, all representing bioinformatics.

The system representing a machine holds 96 vials of pre-frozen material which is ground and fed, to weight, into individual tubes, as 1.4 ml tubes.

A freezer which is used for receiving the cryotemperatures can work by using liquid nitrogen. Such liquid nitrogen pre-freezes the biological material in for example standard 20 ml scintillation vials with reusable caps. These vials are loaded into the pre-chilled machine with the target 1.4 ml tubes. Grinding times can be changed for tougher materials and the input and output data is matched with the bar codes on the target tube blocks. Ground sample can be fed to one or many target tubes, as the operator requires. Grinding and feeding variables are stored in profiles to suit different sample types and standard output configurations. Users can monitor the fed weights and system performance by means of a software during an operation.

Such a system allows biological samples, in particular plant samples, to be homogenized to a fine powder and distributed into small accurately weighed aliquots of pre-selected weight at cryotemperatures for the entire procedure to prevent chemical or biological changes in the biological material. It allows high throughput by handling the biological material being transferred into a fine powder in cryotemperatures, wherein the biological material is to be subsequently extracted and analyzed on a set of different machines for various biological parameters including transcript profiles, protein profiles, metabolite profiles and enzyme activities.

The internal humidity is decreased by using compressed air, which is dried and fed into the chilled chamber to minimize frost built up. A restart facility is available if the power of the machine is interrupted during a long run.

The means for grinding the biological material deposited in the first vessel comprises an oscillating apparatus with a fixing element for fixing the first vessel in a base element and a first oscillating motor, which oscillates the first vessel in at least one direction, preferably in z-direction, with a selectable oscillating frequency and a selectable amplitude. The fixing element comprises a recess in a base element for inserting the first vessel wherein on a bottom of the recess is a spring element for bearing the first vessel springable.

Each first vessel contains in addition a plurality of balls, e.g. three balls of chrome material or chrome coated material, for performing the grinding process during oscillation.

The oscillating motor performs a saw-like movement and allows the attachment of a stainless steel shaft. The oscillating motor is housed within a box which has a foam mould to hold the motor in place. The box is raised and lowered by an SMC cylinder. This raising and lowering action allows firstly vials to be placed into the grinder by a robot arm so that the grinder does not interfere with the robot arm placing the vial and then to bring the grinder down to the correct height for the grinding to occur.

According to a preferred embodiment, the means for loosening the powder resulting from grinding the biological material in the first vessel comprises a pivotable arm, which at one end a holding element for holding the first vessel is arranged. The holding element containing the first vessel is pivotably moveable against a fixed block element in order to loosen the powder in the first vessel by shaking. Such a swing mechanism, which could be L-shaped, enables the pivot movement around a point within the freezer and is operated by a cylinder above the freezer.

According to a preferred embodiment, the means for positioning at least one first opening in the first vessel comprises at least one needle which is arranged on a bottom of a further recess having inserted the first vessel, wherein the recess is arranged in a further base element, and a stamp for pressing the first vessel into the further recess against a spring force of a further spring element is arranged. This process and system component results in a fast and uncomplicated arrangement of a hole at the bottom of the vial by piercing. After the piercing step the spring element press the vial back on an upper position. It is possible to obtain a sharp point pierce. The point is made from a sharpened 2 mm drill bit.

According to a preferred embodiment of the invention, the means for transferring the quantified define portions of powder in a plurality of second vessels comprises a pulling transport element for transporting one of the second vessels to the opening of the first vessel by pulling it up to the lower side of the first vessel, wherein the first vessel is positioned in a powder feeder cup with a second opening at the bottom. Such a powder feeder enables the transfer of the powder from the first to the second vessel by shaking. Therefore, the powder feeder cup is connected with the second oscillating motor for oscillating the powder feeder cup containing the first vessel in order to transfer the powder through the first opening and the second opening in the second vessel.

The second vessel is connected by means of the pulling transport elements with a balance device which measures the weight of the second vessel and the included powder during the transfer step of the powder in order to obtain weighed portions of powder in the different second vessels representing tubes.

The dry air bleeds from the membrane air dryer. This reduces frost build up and is also bled through the vibrating motor (oscillating motor) to stop it from freezing up.

The modus and/or electronic elements of the means are at least partially arranged in a part of a system housing which is separated from another part of the system housing containing cryotemperatures. This avoids the undesired freezing of motor elements and electronic elements, e.g. of the balance.

All means are connected by a robot arm which transports the first vessels and the second vessels between the means among one another and/or between the means and a first and second storing place for storing the first and second vessels. Such storing places for the first vessels within the freezer could be a rack of 96 vials. The rack is located on a separate bed assembly within the freezer to ensure that the samples are at a suitable height for the robot arm. Also on this bed are, for example, six Micronic blocks, each of which contains, for example, 96 1.4 ml Micronic tubes. Also on this bed is a declog station for loosening the powder, the piercer cup and a balance cradle holder.

The robot an passes into the freezer and has two fixtures (pickers) allowing it to pick and place, for example, 20 ml plastic scintillation vials and micronic tubes by suction within the freezer. The suction is provided by a vacuum motor for the vials and vacuum pump for the tubes. The suction is created by applying power to the devices, and the suction is stopped by turning this power off. The vial picker contains an inductive sensor to detect this stainless steel vial cup, allowing the robot to decide whether it has successfully picked the vial. The Micronic tube picker uses a flow sensor to determine the suction flow raise to decide whether the tube has been picked successfully.

Each scintillation vial contains a number of 8 mm ball bearings, typically three of them, and the sample, as plant material, and each vial uses a specially made stainless steel cap to seal in the contents.

Further preferred embodiments can be recognized from the detailed description.

DESCRIPTION OF THE PREFERRED EMBODIMENTS

Figure 1:
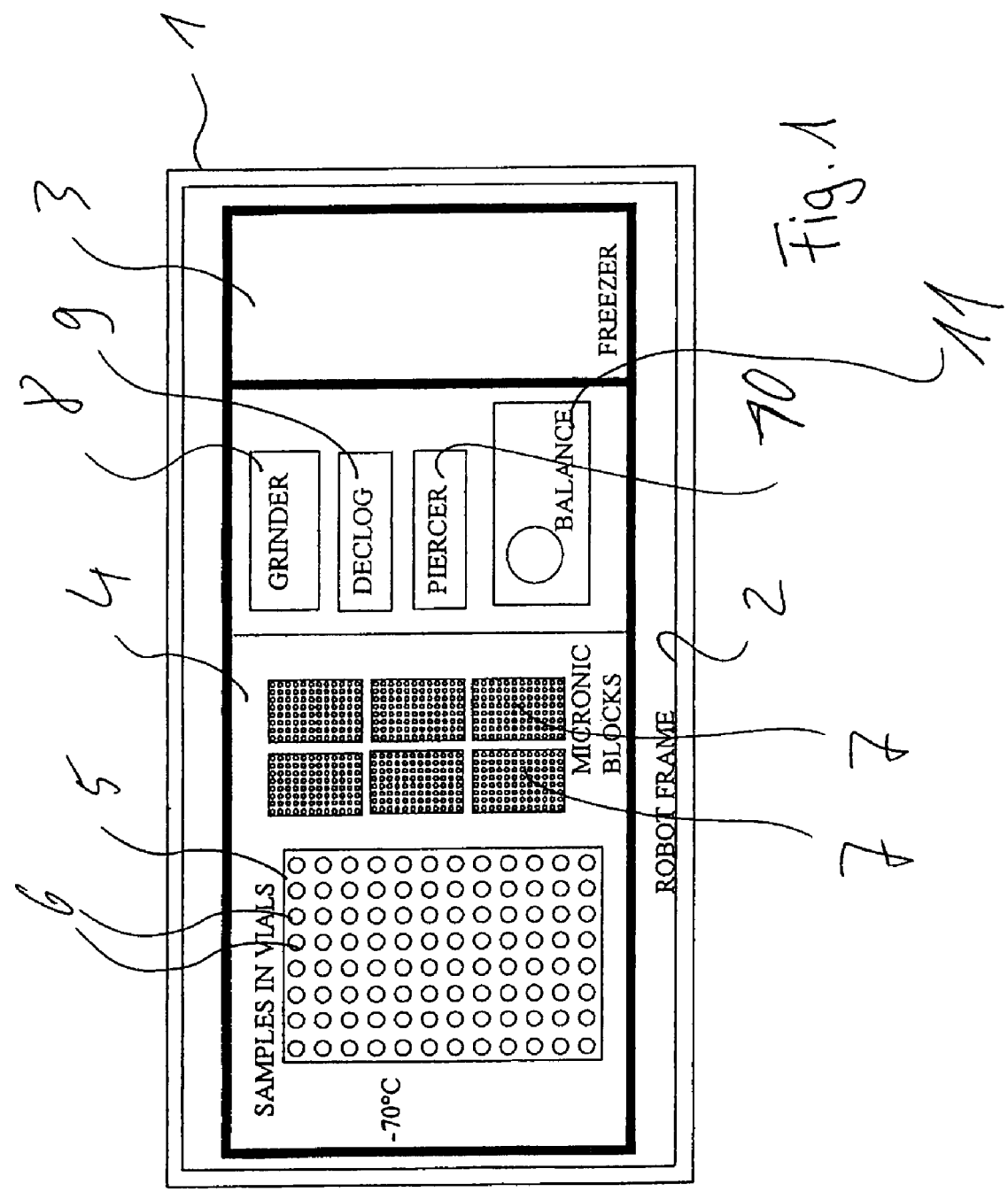
FIG. 1 A top view of the inventive system in schematic version according to one embodiment of the invention.

In FIG. 1 is a top view of the system according to one embodiment of present invention shown. The system has a housing 1, in which a robot frame 2 is arranged. The freezer 3 provides the cryotemperatures of −70° C. in order to perform all working steps at low temperatures.

In a part 4 of the housing 1 first and second storing places 5, 7 which are arranged include the first vessels 6 representing vials and the second vessels representing tubes.

The different stations for grinding, loosening (declog) and positioning an opening (piercer) as well as for transferring the powder including a balance 8-11 are arranged side by side.

Figure 2:
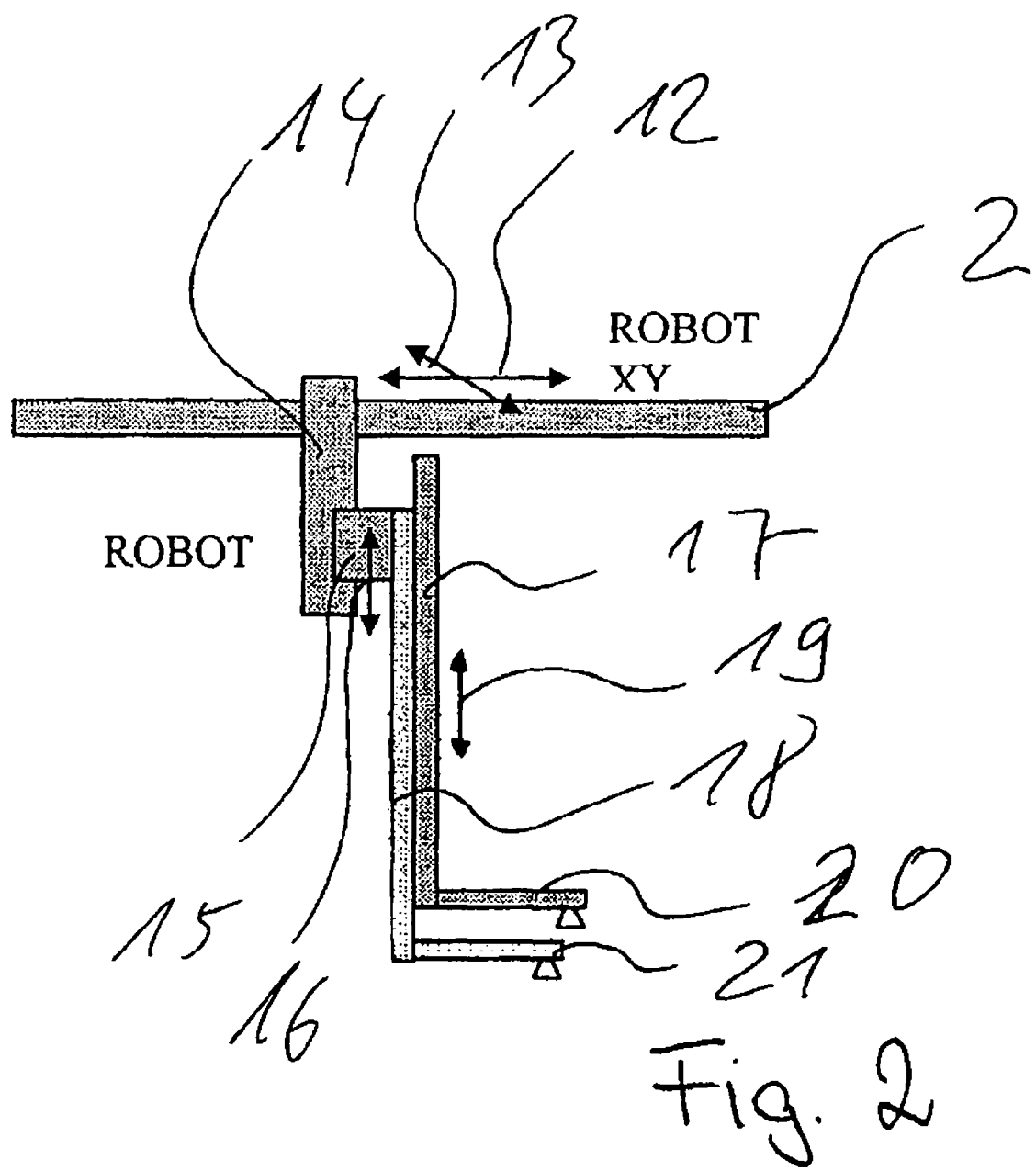
FIG. 2 in a schematic view the robot which is used to handle the vessels in the inventive system.

The robot as shown in FIG. 2 is slideable on a sliding element 2 and can be moved in x- and y-direction 12, 13. The additional part 14 comprises another part 15, which can be moved according to the direction as shown by the reference sign 16.

By moving the part 15 the different arms 17, 18 are moved also, which is shown by the reference sign 19.

Each arm 17, 18 includes a part 20, 21 of the L-shaped form in order to handle the first and second vessels by a different part 20, 21 of different arms 17, 18 respectively.

Figure 3:
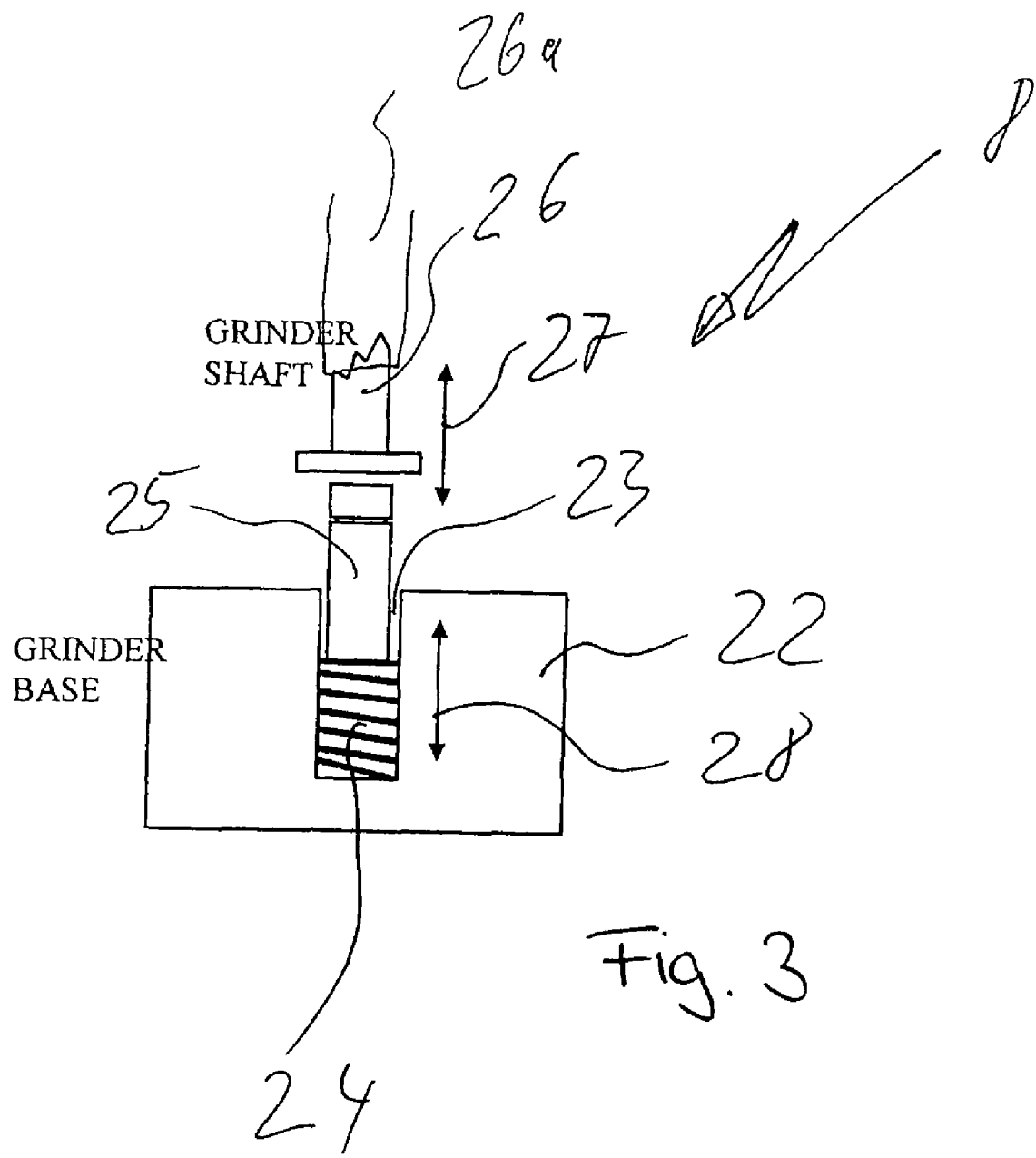
FIG. 3 in a schematic view the means for grinding the biological material.

In FIG. 3 in a schematic view of the means for grinding the biological material, which is for example plant material, in order to obtain powder.

A base element 22 includes a first recess 23 with a spring element 24 at the bottom, in which a first vessel 25, which is a scintillation vial, can be inserted.

The base element could be an aluminium machined cup containing the spring, which is a stainless steel spring. When an oscillating motor 26a is started, the stamp 26 moves the vial in a vertical motion up and down with the compression against an extension of the spring element 24 such that the content of the vial is vigorously shaken. This is shown by reference signs 27, 28.

This action at the temperatures within the cryogenic freezer cause the ball bearings to collide with the frozen sample breaking the sample down into a fine powder. The power is applied to the oscillating motor 26a via a solid state relay for a fixed time period, which could be typically between 30-60 seconds for a good grind. Once a grinding period has elapsed the means for grinding is raised and the vial is picked from the grinder cup 22 by the robot arm.

The oscillating frequency is about 40 Hz at a stroke of, for example, 27 mm. The ball bearings break the plant sample within the vial during the grind process. A metal cup has been employed to avoid shattering the cup.

Figure 4:
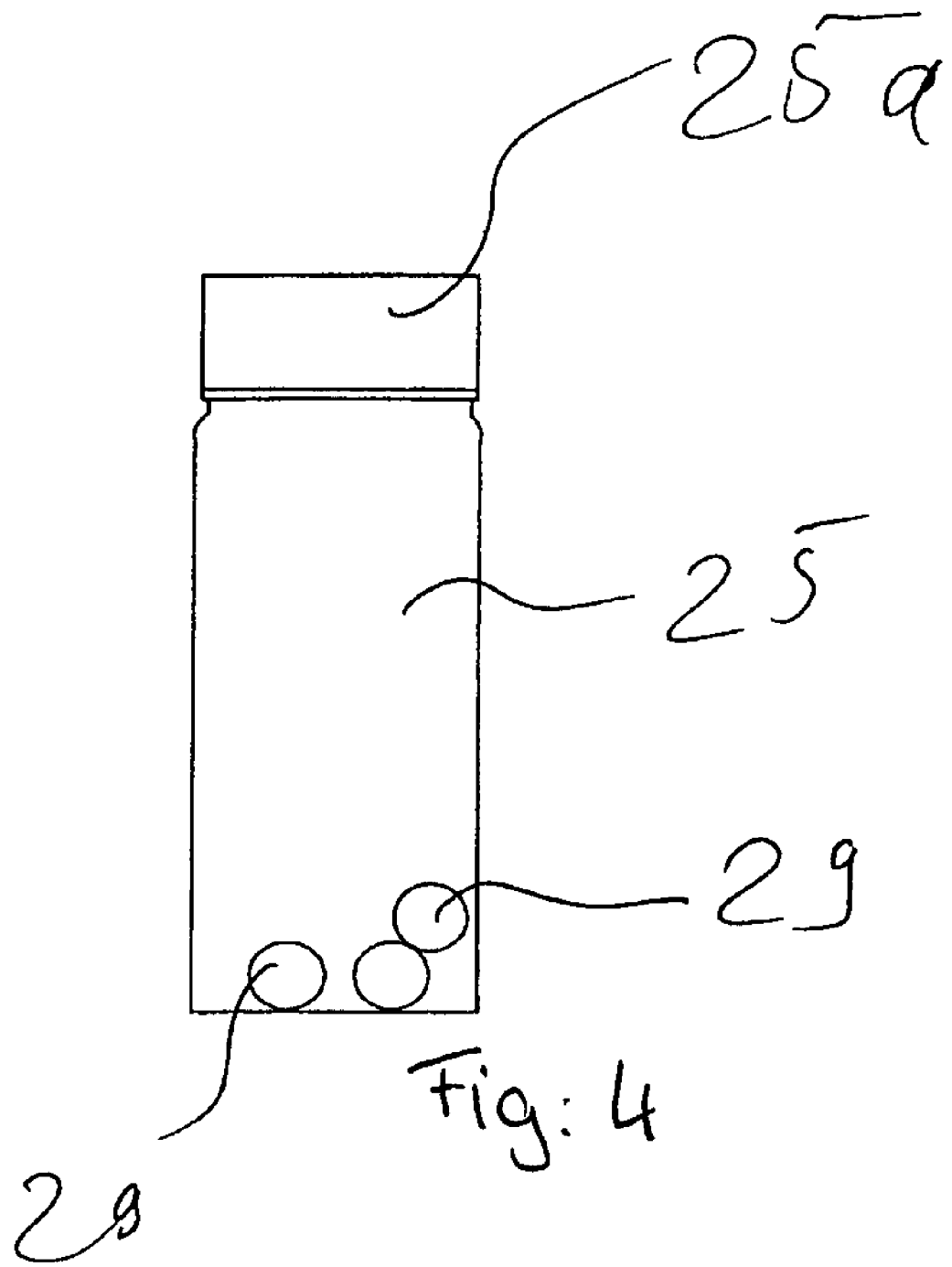
FIG. 4 a first vessel with balls in a schematic view.

In FIG. 4 is shown the first vessel representing a scintillation vial 25 with a cap 25a and the balls 29 which could have a diameter of, for example, 8 mm.

Figure 5:
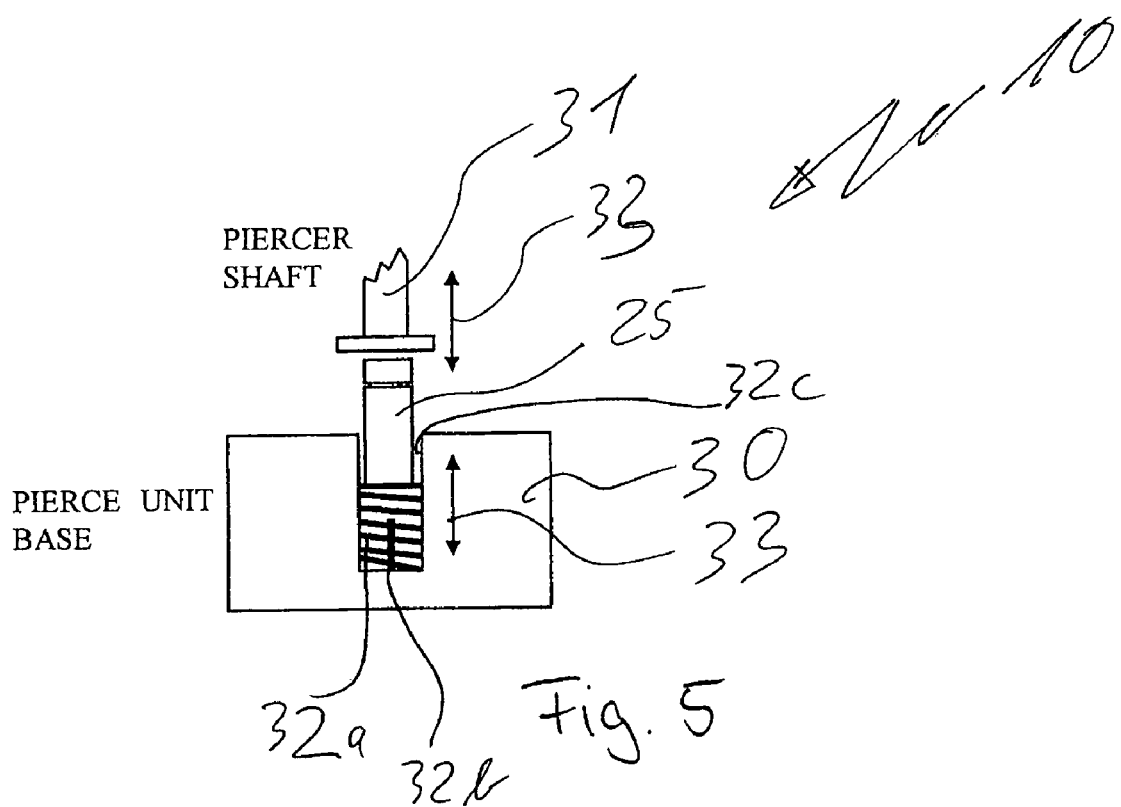
FIG. 5 in a schematic view the means for positioning the first opening at the first vessel.

In FIG. 5 is shown in a schematic view of the means for positioning a first opening at the bottom of the vial 25.

The robot moves the vial 25 to the station for positioning the opening/hole and places the vial into a basis element 30, which could be a piercer cup located on the robot bed. The piercer cup 30 consists of a recess 32c containing a small stiff spring element 32a and a needle 32b at the bottom, crafted from a 2 mm drill bit and sharpened to a point.

A force is applied to the vial in the piercer cup 30 by a cylinder 31 mounted above the freezer. This force compresses the spring element 32a forcing the needle 32b point through the bottom of the vial. When the force is removed and the cylinder returned back to its original position the stiff spring element 32a pushes the vial 25 back off the sharpened point of the needle 32b. The robot then picks the vial 25 from the cup using the suctions. The movement is shown by the reference signs 33. The recess is shown by reference sign 32c.

Figure 6:
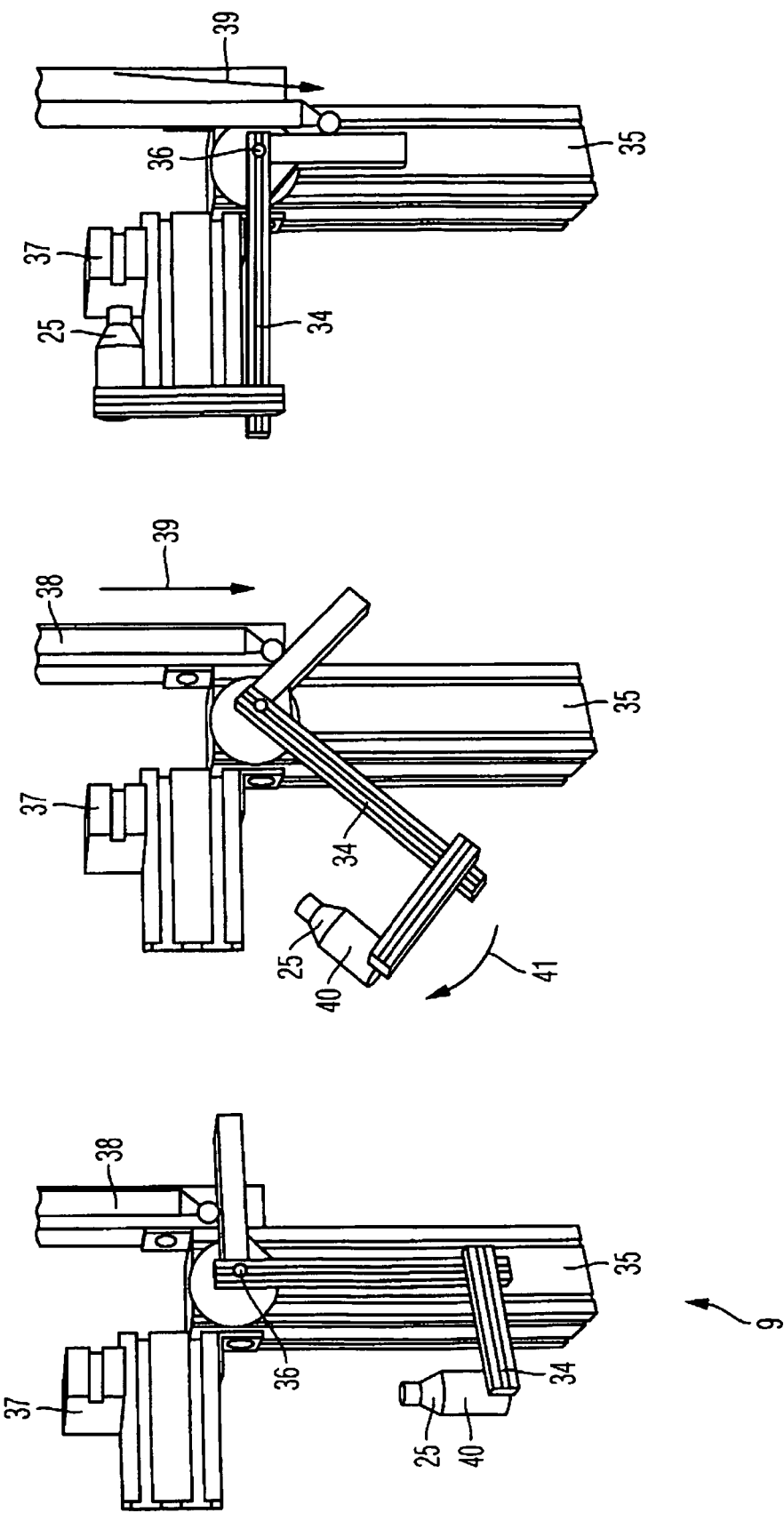
FIG. 6 the process of the means for loosening the powder in the first vessel according to the present invention.

In FIG. 6 is shown the process of the means for loosening the powder in the first vessel/vial 25 in three different steps. The vial 25 is positioned in a cup holder 40 mounted to the end 34 of an L-shaped swing mechanism. This mechanism pivots around a point 36 as it is shown by the reference signs 41.

The pivot movement is within the freezer and is operated by a cylinder 38 above the freezer.

When actuated, the mechanism raises the vial 25, swinging it through an arc to almost horizontal and causes the vial 25 to collide with beam 37 which is fixed at the main feed element 35. The movement of the cylinder is shown by the reference sign 39.

This collision action is used to loosen the powder inside the vial 25 both after a grinding and during vipro-feeding. Both these actions have been found to compact the powder, which causes it to feed poorly. This process counteracts the compacting of the powder. The loosening step is completed after typically five actuations of the mechanism. The vial 25 is picked from the cup 40 by the robot arm using the suction method as already described.

Figure 7:
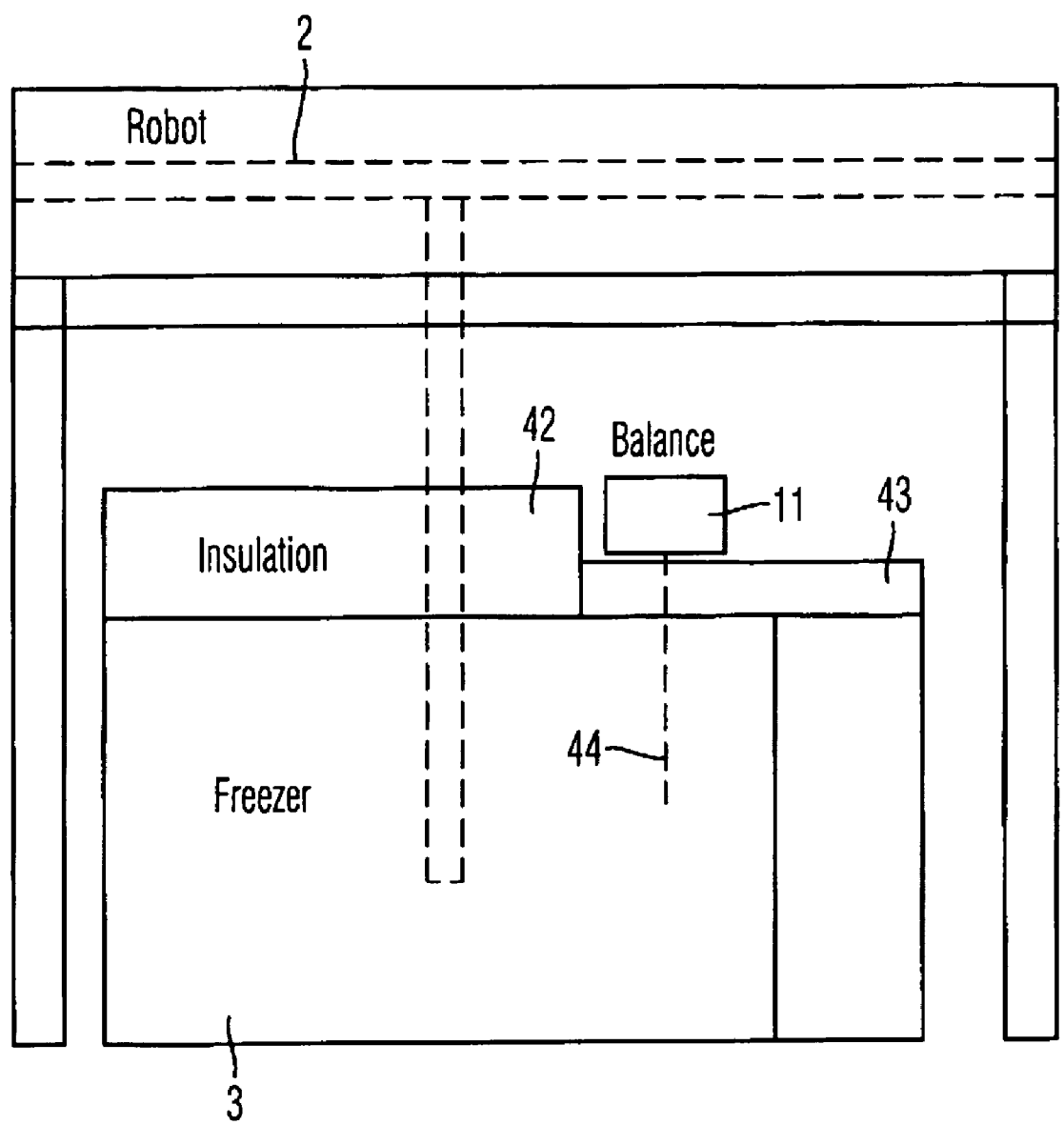
FIG. 7 in a schematic view the construction of the freezer, the balance and the robot according to the present invention.

In FIG. 7 is shown in a schematic view the balance as well as parts of the freezer and the insulation material and the robot. The freezer 3 can produce temperatures to −85° C. To maintain the temperature of the freezer, the walls are extended upward with the 80 mm thick foamed insulation panels. The balance is housed in an ambient temperature area above the freezer and can be raised and lowered on its one axis.

Access to the freezer 3 for maintenance purposes is available through panels at the front and rear.

The work bed within the freezer will try to move during the repeated cooling cycles of the system. It is mounted in the freezer with adjustable feet on all sides so it is always positioned correctly. A corner cut-out will allow access to remove any water after a prolonged period of use. The bed will be raised on strips to allow the water to circulate.

The freezer attempts to maintain the temperature as set on the control panel. This temperature is set at −75° C., preferably the freezer is set at −66° C.

The balance 11 is separated from the freezer 3 by an isolation material 43 and comprises further elements which are connected to the balance in the freezer area, which is shown by a reference sign 44.

Figure 8:
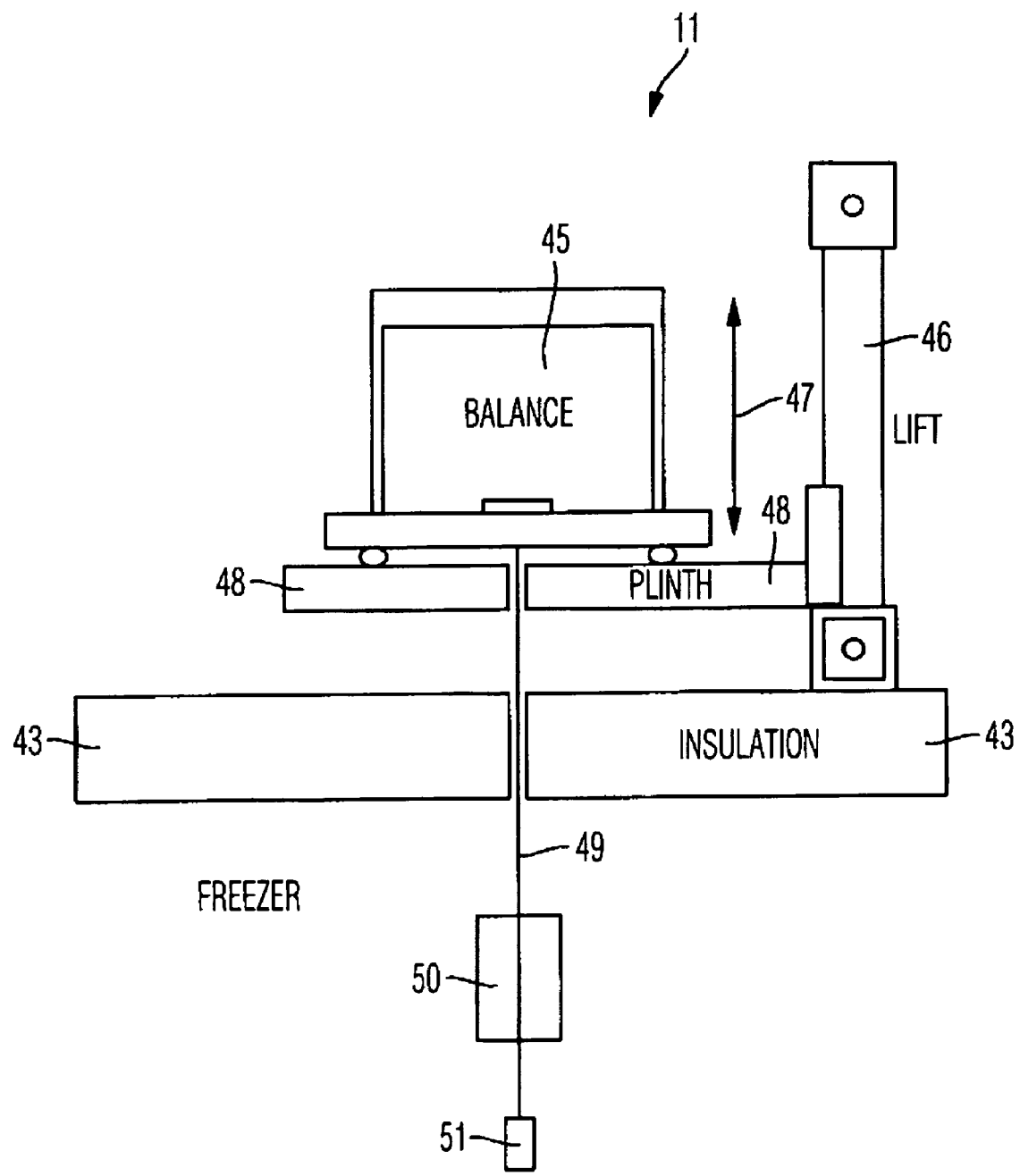
FIG. 8 in a schematic view the means for weighing the powder and the vessels.

In FIG. 8 is shown the means for transferring and weight the powder from the first vessel to the second vessel.

Once the robot has placed the vial 25 with ground sample and pierced hole into the powder feeder cup, it goes and picks a Micronic tube 51 from the Micronic racks mounted on the bed using suctions through the Micronic pick up. The cube 51 is placed onto the balance cradle, which is located on the robot bed and is shown in FIG. 9 by reference sign 58.

Figure 9:
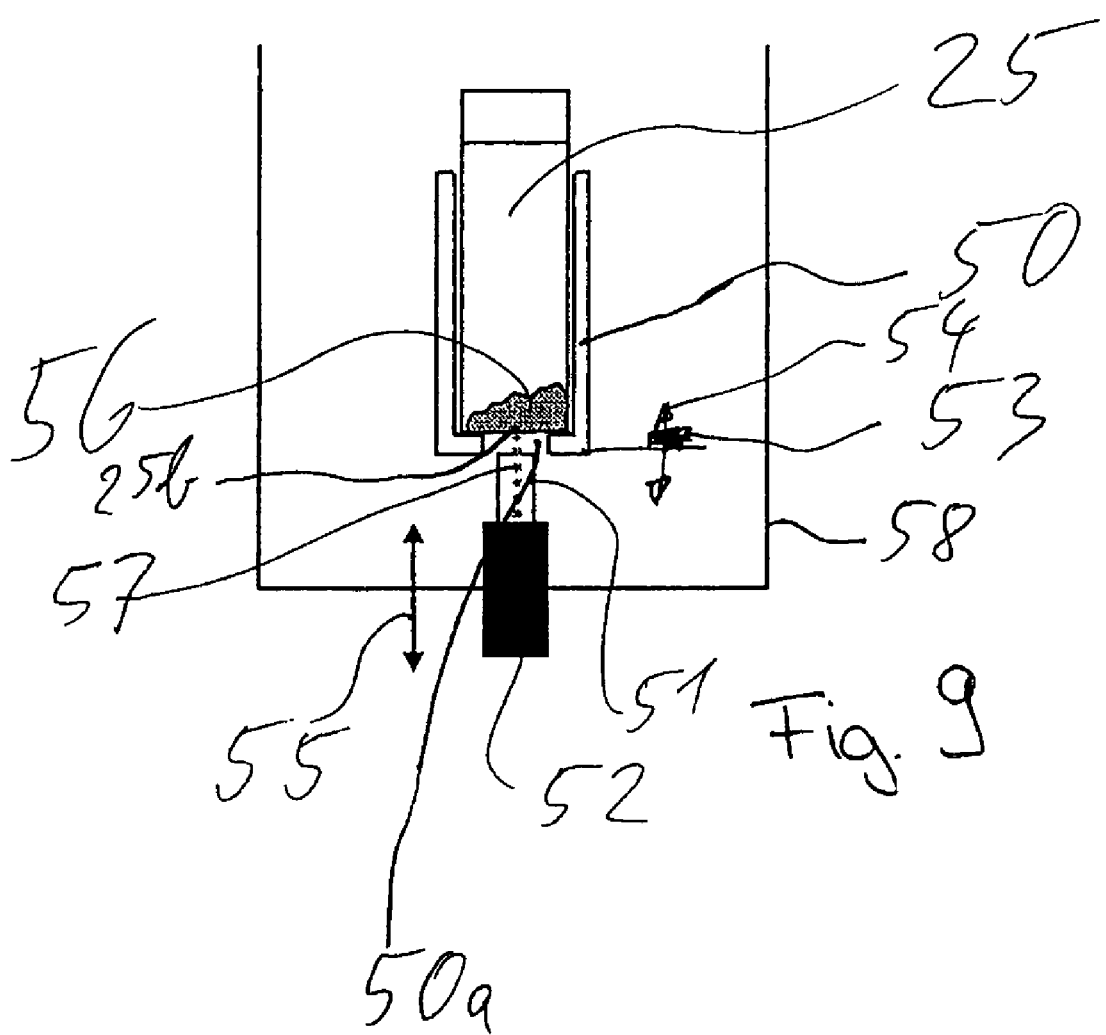
FIG. 9 the parts of the means for transferring the powder in a schematic view to the present invention.

The balance 45 is connected with the pulling element 58 as shown in FIG. 9, and the cup 50. The balance 45 is mounted to stepper motor 46 driven by screw axis, allowing it to be raised and lowered as it is shown by reference sign 47.

Basically, the vial 25 is placed into the powder feeder cup 50 by the robot. The cup 50 has a hole 50a in the bottom as it is shown in FIG. 9.

This hole is specifically shaped to suit the positioning of the Micronic tubes 51, which is placed in a cup 52.

The tubes are raised into position by the driven balance axis 46. An oscillating motor 53, which moves according to reference sign 54 as it is shown in FIG. 9, with control means is rotated. The speed of the rotation is adjustable via a potentiometer on the side of the robot. The offset weight causes the whole assembly to vibrate and the vial 25 with pierced hole in the bottom to vibrate. This creates a stream of powder 57 to fall from the vial 25 through the holes 25b and 50a into the Micronic tube 51 below.

The movement of the frame 58, which is performed by the lift 46, is shown by the reference sign 55.

The motor speed of rotation can be varied to change the level of vibration to suit the type of plant material and feed rates of the sample powder.

The balance axis 49 raises the balance and takes a zero reading, which means the balance is "tared". The balance 45 then raises to its uppermost position, which pulls the Micronic tube 51 into the bottom of the powder feeder cup 50. The motor is vibrated for a small period of time, which is typically 0.5 sec. The powder falls through the pierced hole in the vial and into the Micronic tube 51. The balance is moved down to take the weight reading. This gives the amount of the material fed in 0.5 s. The computer program calculates the feed rate and calculates the time needed to feed the correct weight. The feed is then re-performed for this period and a further weight reading is made. The process continues until the correct weight is achieved or an overfeed occurs. The balance 45 moves back down to its down position and the Micronic tube 51 is picked and returned to the rack by the robot arm. The weight value is stored in the robot output file on the PC and the screen is updated to indicate to the operators the current status of the run.

The pierced hole has a diameter of around 1.5 mm and the internal diameter of the Micronic tube is 6.8 mm.

LIST OF REFERENCE SIGNS 1 system housing
4 another part
8, 9, 10, 11 means
6, 25, 51 first vessel
23 recess/fixing element
24 spring element
25b first opening
26a first oscillating motor
27, 28 z-direction
29 balls
31 stamp
32a spring element
32b needle
32c the first recess
34 pivotable arm
37 fixed block element
40 holding element
45 balance device
50a second opening
51 second vessel
52 cup
56, 57 powder
58 pulling transport element

What is claimed is:

1. System for producing quantified defined portions of powder from at least one biological material at cryotemperature, comprising:
    means for grinding the biological material deposited in at least one first vessel to the powder;
    means for loosening the powder resulting from grinding the biological material in the first vessel;
    means for positioning at least one first opening in the first vessel, and
    means for transferring the quantified defined portions of powder in a plurality of second vessels by using the first opening as a transfer way.

2. System according to claim 1, characterized in that the means for grinding the biological material comprises an oscillating apparatus with a fixing element for fixing the first vessel and a first oscillating motor, which oscillates the first vessel in at least one direction, with a selectable oscillating frequency and a selectable amplitude.

3. System according to claim 2, characterized in that the fixing element comprises a recess for inserting the first vessel, wherein a spring element for bearing the first vessel springable is arranged on a bottom of the recess.

4. System according to claim 1, characterized in that each first vessel contains in addition a plurality of balls for performing the grinding process during oscillation.

5. System according to claim 1, characterized in that the means for loosening the powder comprises a pivotable arm which has at one end a holding element for holding the first vessel, wherein the holding element containing the first vessel is pivotable movable against a fixed block element in order to loosening the powder in the first vessel by shaking.

6. System according to claim 1, characterized in that the means for positioning at least one opening in the first vessel comprises at least one needle, which is arranged on a bottom of a further recess having inserted the first vessel, wherein a stamp for pressing the first vessel in the first recess against a spring force of a further spring element is arranged.

7. System according to claim 1, characterized in that the means for transferring the quantified defined portions of powder in a plurality of second vessels comprises a pulling transport element for transporting one of the second vessels to the opening of the first vessel by pulling it up to the lower side of the first vessel, wherein the first vessel is positioned in a powder feeder cup with a second opening at the bottom.

8. System according to claim 7, characterized in that the powder feeder cup is connected with a second oscillating motor for oscillating the powder feeder cup containing the first vessel in order to transfer the powder through the first opening and the second opening in the second vessel.

9. System according to claim 7, characterized in that the second vessel is connected by means of the pulling transport element with a balance device which measures the weight of the second vessel and the included powder during the transfer step of the powder.

10. System according to claim 1, characterized in that the system contains a freezer.

11. System according to claim 10, characterized in that the motors and/or electronic elements of the means are at least partially arranged in a part of a system housing which is isolated from another part of the system housing containing cryotemperatures.

12. System according to claim 1, characterized in that the means for grinding the biological material, the means for loosening the powder, the means for positioning at least one first opening and the means for transferring the quantified defined portions of powder are connected by a robot arm, which transports the first vessels and the second vessels in x-, y- and/or z-directions between the means among themselves and/or between the means and a first and second storing place for storing the first and second vessels.

13. The system of claim 2, wherein the direction of oscillation of the first vessel is in the z-direction.

* * * * *